United States Patent [19]

Suzuki et al.

[11] 4,106,986

[45] Aug. 15, 1978

[54] MANUFACTURE OF EPOXIDE USING A MICROORGANISM

[75] Inventors: Shuzo Suzuki, Sayama; Keizo Furuhashi, Toda; Akira Taoka, Urawa, all of Japan

[73] Assignee: Bio Research Center Company, Ltd., Tokyo, Japan

[21] Appl. No.: 842,029

[22] Filed: Oct. 14, 1977

[30] Foreign Application Priority Data

Jun. 24, 1977 [JP] Japan ................... 52-75127

[51] Int. Cl.² .............................................. C12D 13/00
[52] U.S. Cl. ................. 195/28 R; 195/51 R
[58] Field of Search ............ 195/28 R, 51 R

[56] References Cited

U.S. PATENT DOCUMENTS

| 3,440,141 | 4/1969 | Douros et al. | 195/28 R |
|---|---|---|---|
| 3,508,927 | 4/1970 | Herndon et al. | 195/28 R |
| 3,709,783 | 1/1973 | Tanaka et al. | 195/28 R |
| 3,871,956 | 3/1975 | Azarowics | 195/28 R |

*Primary Examiner*—Alvin E. Tanenholtz
*Attorney, Agent, or Firm*—Donald R. Cassady

[57] ABSTRACT

The production of epoxide from $\alpha$-olefin or $\alpha,\omega$-diene using an epoxide producing microorganism that belongs to Nocardia genus, wherein said microorganism is cultured aerobically in a medium containing more than one straight-chain $\alpha$-olefin and/or straight-chain, $\alpha,\omega$-diene chosen from $\alpha$-olefins having 4 to 20 carbon atoms and $\alpha,\omega$-dienes having 4 to 20 carbon atoms, or cells obtained by culturing said microorganism in a medium containing assimilable carbon sources is allowed to react aerobically in a medium containing more than one $\alpha$-olefin and/or $\alpha,\omega$-diene selected from said straight-chain $\alpha$-olefins and/or $\alpha,\omega$-dienes, and produced $\alpha$-epoxide or $\alpha,\omega$-diepoxide or a mixture of these is separated and harvested.

2 Claims, No Drawings

MANUFACTURE OF EPOXIDE USING A MICROORGANISM

SUMMARY OF INVENTION

This invention is concerning the production of epoxides such as α-epoxides and α,ω-diepoxides using a microorganism. These epoxides are useful raw materials of surfactant and paints and they are also used widely as raw materials or intermediates of various organic chemicals. However, there has not been any report about the production of α-epoxide, α,ω-diepoxide or a mixture of these in high yields using a microorganism. It has now been found that a microorganism that belongs to Nocardia genus can produce α-epoxides or α,ω-diepoxides or a mixture of these from α-olefins or α,ω-dienes as a carbon source.

As described above, this invention is characterized by using an epoxide-producing microorganism to manufacture α-epoxides or α,ω-diepoxides or a mixture of these in high yields.

The microorganism employed in this invention was separated from the soil collected in the oil field area in Japan and harvested. It can be designated as *Nocardia corallina* var. Taoka or one affinitive to *Nocardia corallina* by collating its properties with Bergey's Manual of Determinative Bacteriology, 8th Edition, 1974. This microorganism was deposited with Agency of Industrial Science and Technology, Fermentation Research Institute of the Ministry of Industrial Trade and Industry, Japan as FERM-P-4094 on June 15, 1977.

The microorganism has also been deposited with American Type Culture Collection and bears ATCC No. 31338.

Source:
Soil
Characterization:
Morphology

The bacterium is a gram positive (modified Hucker's Method), non-acid fast (Ziehl-Neelsen's Method), rod-shaped microorganism displaying a general coryneform nature. Individual cells are 0.5-1 × 2-3 nm in stained smears but characteristically the cells occur in pairs, long filaments (100-200nm) and masses. Cellular morphology is quite variable and includes club-shaped, Y-shaped and coccoidal forms. After 12-14 hours incubation on nutrient media at 28° C, primary branching of the cells was noted. After 18-20 hours, septa were formed at random in filamentous cells, and the cells divided by fragmentation. Preparations from liquid media consisted of masses of cells composed essentially of long, tapered, paired cells (0.5-1 × 6.8 nm) arranged in a jackstraw fashion. The cells stained irregularly with alkaline methylene blue (Loeffler's) which is typical of coryneform bacteria.

No endospores.
No motility observed in hanging drop preparations.

Cultural features

The bacterium is not fastidious and will grow rapidly and abundantly upon ordinary bacteriological culture media if the conditions are aerobic. Stock cultures were maintained upon TGY agar slopes [trypticase (BBL), 0.2%; peptone (Difco), 0.1%; yeast extract (Difco), 0.1%; glucose; 0.5%; $MgSO_4$, 0.02 M; phosphate buffer to give a final concentration in the medium of 0.02 M and pH 7] and culture descriptions are for growth upon TGY agar.

Slope cultures were opaque, orange becoming pink and sometimes dark red, filiform and glistening. Colonies usually were 2-3 mm diameter, circular, shiny, smooth consistency, opaque, pulvinate, intensely pigmented orange becoming dark pink. Growth was evident within 12 hr., 30° C., and colonies were well formed within 24 hr. Maximum pigmentation required 4-6 days.

Growth in TGY broth with static conditions of incubation, 30° C., was scant and granular never uniformly turbid. A patchy pellicle forms slowly and settles to produce an abundant sediment. Pellicle is pigmented a dark red. Liquid cultures incubated with constant shaking are uniformly turbid and an abundant sediment accumulates. These latter are faintly pigmented.

Physiological attributes

Oxygen relationships

No growth on media incubated anaerobically (alkaline-pyrogallol technique) and surface growth only in stab and static liquid cultures.

Catalase positive.

Temperature tolerance

Growth occurred in the temperature range from 5° C. to 40° C. and was abundant at 30° C. Ability to grow at temperatures above 40° C. was not tested.

The bacterium did not survive heating at 65° C. for 30 minutes.

Tolerance to NaCl

Abundant growth in TGY broth containing 3% and 5% NaCl, slight growth in the presence of 7% NaCl but none in 10%.

Resistance to antibiotics

Tests of resistance to antibiotics were made by the disc assay method on TGY agar plates. Generally growth of the bacterium was inhibited by antibiotics which is typical fom gram positive bacteria. The exception was the tolerance to nystatin and this too would be expected for microorganisms in which sterols are generally absent from their membranes. Growth was inhibited by: penicillin (10 units), amphicillin (10 mg), streptomycin (10 mg), aureomycin (30 mg), cephalothrin (30 mg), gentamycin (10 mg) and sulfadiazine (300 mg). Growth was not inhibited by nystatin (100 units).

Hydrolytic ability

The bacterium did not hydrolyze starch, cellulose or gelatin when grown in nutrient media containing these substrates. TGY agar was supplemented with either starch or gelatin to give a final concentration of 1%. Disappearance of starch was tested for using Lugol's iodine solution and of gelatin using saturated $(NH_4)_2SO_4$ solution. Cellulose hydrolysis was tested for by placing a sterile strip of filter paper into an inoculated tube of TGY broth and then incubating the culture at 30° C. with constant shaking. In this classical test cellulolytic ability is indicated by disintegration of the cellulose strip. Test for hydrolytic ability were made after 4 days incubation, 30° C.

Fermentative ability

The ability of the bacterium to ferment selected organic compounds was tested by adding aseptically a known amount of a previously sterilized organic compound to sterile phenol red broth base (Difco). The media was inoculated with a single drop of a suspension of the bacterium prepared from a 24-48 hour-old TGY slope culture. Fermentability was determined by acid production after 48 hr. incubation, 30° C. Growth occurred in all the cultures and all had pellicles form. Only two sets of cultures showed acid reactions and these contained either added glucose or mannitol. The organic compounds tested were glycerol, xylose, glucose, fructose, mannose, galactose, sucrose, lactose, cellobiose, maltose and mannitol.

A replicate of culture tubes containing the phenol red broth medium individually supplemented with the organic compounds above, was incubated with constant shaking, 48 hr., 30° C., to test ability of the bacterium to produce acid from an organic compound under aerobic conditions of incubation. Acid reactions were produced only from glucose, fructose and mannitol.

Nutritional requirements

The nutritional requirements of the bacterium were tested in terms of its ability to grow in a chemically known basal medium modified with selected supplements. Two properties were sought, the minimum, primary nitrogen source and the need for accessory growth substances. The primary carbon source was glucose. The unsupplemented basal medium consisted of glucose, 0.5%; dissolved in 0.02M phosphate buffer, pH 7, which contained $MgSO_4$ in a final concentration of 0.015M. The basal medium was supplemented with an inorganic source of nitrogen ($NH_4Cl$, 0.2% final concentration), a single amino acid (asparagine, 0.2% final concentration), a mixture of amino acids (acid-hydrolyzed casein, 0.2% final concentration), or a mixture of peptides (enzyme-hydrolyzed casein, 0.2% final concentration). One set of cultures for each nitrogen source was further supplemented with yeast extract (0.005% final concentration) as a general source of accessory growth substances. The individual culture tubes were inoculated with one drop of the bacterium suspension in phosphate buffer, 0.02M, pH 7. The bacterium grew well with each nitrogen source with or without added yeast extract. Since the medium containing glucose and $NH_4Cl$ without further supplementation is quite satisfactory for growth, the bacterium is nutritionally very efficient.

The bacterium produced nitrite from nitrate in nitrate and succinate-nitrate broths. No ability of nitrate respiration was observed. It did not produce indole or acetylmethylcarbinol. It produced hydrogen sulfide slightly. Methyl red reaction was negative.

The lack of nutritional fastidiousness was confirmed in other nutritional studies to determine the need for accessory thiamin. While no accessory growth factors were required to support growth of the bacterium in a basal medium containing $NH_4Cl$, glucose, phosphate buffer and $MgSO_4$, either a mixture of thiamine-HCl, biotin, riboflavin, phosphate, pyridoxine-HCl and folic acid, or yeast extract (0.005%) was needed for heavy growth. Thiamine supplementation alone did not result in heavy growth.

Pigmentation

The subcultures of the bacterium which were studies were invariably pigmented in the color range orange to a coral pink. The casual work which has been done to characterize the pigmentation indicates it is due to a mixture of carotenoids the principal one of which has an electronic absorption maximum at 455 nm in diethyl ether. The spectral curve lacks fine detail and this together with the wavelength of the maximum absorption suggests a chromphore of 11 conjugated double bonds extending into a $\beta$-terminal ring system. Thin-layer chromatography showed the mixture of presumed carotenoids consisted of 5 constituents. $R_f$ values indicate one constituent is nonpolar and four have polarities ranging from that expected for a dihydroxy carotenoid to those with three hydroxyl groups. These opinions are generalizations at best.

Nucleotide base ratio analysis

The bouyant density method was used to establish the guanine + cytosine mole percent DNA nucleotide base ratio (% G+C). The bouyant density of DNA from the bacterium is 1.7285 g/cm$^3$ which is equivalent to 69.9% mole percent G+C. The reference DNA preparations and the buoyant densities for each were *Escherichia coli*, 1.710 g/cm$^3$ and bacteriophage $\phi$25, 1.742.

Cell wall

The principal amino acid in the cell wall is meso-diamino-pimelic acid.

Taxonomic recommendation

The bacterium is related to bacteria which have been classified in Part 17, Actinomycetes and Related Organisms, Bergey's Manual of Determinative Bacteriology, 8th Edition, Williams and Wilkins, Baltimore, 1974. The gross morphological features of the bacterium resemble generally those associated with both coryneform and nocardioform bacteria. The decisive phenetic property differentiating the two is whether a bacterium shows the mycelial growth of Nocardia at some stage of cultural development since coryneform microorganisms display only rudimentary branching not extensive enough to be regarded as mycelial in nature. Absence of mycelial development, however, does not automatically evoke assignment to Corynebacterium since mycelial development in Nocardia is not always pronounced.

Microscopic study of developing cultures of the bacterium has shown a highly branched morphology in young cultures (>24 hr., 30° C.) followed by coryneform morphology at 24 hr. It is assumed that the latter originated from fragmentation of the mycelia of the younger cultures. On this basis the bacterium may be assigned to the genus Nocardia. Physiological properties, the occurrence of meso-diaminopimelic acid in the cell wall and the DNA nucleotide base ratio (moles % guanine + cytosine, G+C) are compatible with this taxonomic assignment.

The bacterial genus Nocardia is divided into three morphological groups, I, II, and III, to encompass the morphological transition from the coryneform morphology, which is pleomorphic with only rudimentary branching, to extensive mycelial formation and some aerial hyphae. Bacterium can be placed in morphological Group II of Nocardia. The majority of species of this Group previously have been collected into a common taxon termed the "rhodochrous complex" by Goodfellow (Goodfellow, M. Numerical taxonomy of some nocardioform bacteria, J. Gen. Microbiol. 69, 33–80, 1971. See also, Goodfellow, M., A. Fleming and M. J. Sackin, Int. J. System. Bacteriol., 22, 81–98, 1972). The species of morphological Group II of Nocardia (Bergey's Manual, 8th Edition, loc. cit.) which were included by Goodfellow in his rhodochrous complex are *N. opaca, N. rubra, N. salmonicolor, N. lutea, N. rubropertincta* and *N. corallina*. Actually the complex which comprised 283 nocardioform cultures, was divided into 15 phenetic clusters as a result of the taxometric study and those now included as species in Group II all were in Cluster 14. This phenetic group was further divided into 8 subclusters and the Nocardia species listed above all were in subcluster 14C. Actually the phenetic differences in Cluster 14C could be said to be too minor for construction of more than one species to represent the taxon and this is implied in the discussion of the present taxonomic arrangement for Group II. The implication is that the above species are closely related and that *N. corallina* is representative of the group.

The taxonomic recommendation for the bacterium is *Nocardia corallina* var. Taoka.

A wide range of assimilible carbon sources can be used as substrate for the microorganism. Preferably sources, however, include the α-olefins having 3 to 20 carbon atoms and/or α, ω-dienes having 4 to 20 carbon atoms.

Also, carbon sources used in this invention can include other hydrocarbons in addition to α-olefins and/or α,ω-dienes which are indispensable for the production of epoxide as described above.

These additional carbon sources may be added with the olefins as a component of a medium is separation of the component which is difficult to do by usual methods can be carried out easily when α-olefins, α,ω-dienes or a mixture of these are converted to 1,2-epoxide. Thus, for example, separation of paraffins and α-olefins can be accomplished by reaction with the microorganisms as shown in this invention.

In a medium containing said carbon sources, nitrogen sources and inorganic salts are added, and then the above mentioned microorganism is inoculated to cultivate by agitation or shaking under an aerobic condition.

The substances added into the medium as nitrogen source can be anything that the microorganism is able to assimilate, for example, ammonium phosphate, ammonium chloride, ammonium sulfate, ammonium nitrate, urea, aqueous ammonia and/or various kinds of amino acids. One kind out of these will suffice but a combination of more than two will also do.

As inorganic salts, potassium phosphate, sodium phosphate, magnesium sulfate, manganese sulfate, ferrous sulfate and/or calcium chloride are used.

Nutrients such as vitamins and yeast extract may be added to said medium in order to stimulate the growth of the microorganism.

Besides cultivation of the microbe in the above mentioned medium to produce epoxide, this invention also includes preculture of said microbe in a medium containing assimilable carbon source, for example, glucose, sucrose, sorbitol, glycol, n-paraffin, α-olefin and propylene, then allowing the resultant grown cells to react aerobically in the medium of the same compositions as mentioned above.

This two-step process of cultivation, then reaction is conducted in all cases under an aerobic condition by passing an oxygen-containing gas as for example air or a gas resembling air into the medium for 1 to 6 days at 5° to 40° C. or 20° to 38° C. being desirable keeping pH level at 6 to 8, and usually under the normal pressure but may be carried out under increasing pressure depending on the carbon source used as substrate.

As described above, this invention produces advantageously α-epoxide, α,ω-diepoxide or a mixture of these from said α-olefin and/or α,ω-diene as raw material which is obtainable at comparatively cheap price. It is believed that this invention contributes a great deal to manufacture of epoxides on a commercial scale.

DETAILED DESCRIPTION OF PREFERRED EMBODIMENT

The present invention will now be described specifically with reference to preferred embodiment.

EXAMPLE 1

| | |
|---|---|
| di-Ammonium hydrogen phosphate $(NH_4)_2HPO_4$ | 4g |
| di-Sodium hydrogen phosphate $Na_2HPO_4 \cdot 12H_2O$ | 2.5g |
| Potassium di-hydrogen phosphate $KH_2PO_4$ | 2.0g |
| Magnesium sulfate $MgSO_4 \cdot 7H_2O$ | 0.5g |
| Ferrous sulfate $FeSO_4 \cdot 7H_2O$ | 30mg |
| Calcium chloride $CaCl_2 2H_2O$ | 60mg |
| Manganese chloride $MnCl_2 \cdot 4H_2O$ | 60μg |
| Yeast extract | 200mg |

The above components were dissolved into 1 liter deionized water. pH of the obtained solution was 7.2 The solution was pipetted 50ml into each 500ml Sakaguchi flasks and was sterilized at 115° C for 15 minutes.

Next, 2 loopfuls of *Nocardia corallina* var Taoka, B-276 (FERM-P-4094) which had been cultured in a nutrient-glucose agar at 30° C. for 24 hrs. were inoculated to each solution prepared as described above, and were autoclaved or filtered through a milipore filter.

Carbon sources as substrate were added properly so that the total amount of them would make 0.5g; then a cultivation was carried out aerobically. In the case propylene and butene-1 were used as substrate, said Sakaguchi flasks were closed up tight, reduced pressure 15 cm Hg and a suitable volume of gas was introduced to put the pressure back to the original one.

After 5-day cultivation at 30° C., obtained broth was analyzed by gaschromatography in order to identify and quantify the produced epoxides.

The results are shown in Table 1.

EXAMPLE 2

Preparation of suspension for the microbe to use for a reaction.

Solution having the same composition as the one in Example 1 was distributed 200ml each to 3-liter vessels for cultivation, added with 2g of glucose and sterilized at 115° C. for 15 minutes. *Nocardia corallina* B-276 (FERM-P-4094) which had been cultured on nutrient-glucose agar was inoculated 8 loopfuls to the above mentioned medium in order to cultivate aerobically at 30° C. for 24 hrs. After cultivation, cells were centrifuged and washed with 0.05M phosphate buffer at pH 7; then the cells were suspended on new 0.05M phosphate buffer at pH 7 so that the number of the cells on the suspension were $3 \times 10^9$/ml. This was made a suspension for the reaction.

Reaction

The suspension prepared as described above was pipetted 20ml each into 500ml Sakaguchi flasks. To this, 0.2g of α-olefins or α,ω-diolefins as substrate, as shown in Table 2, were added in order to carry out a reaction aerobically at 30° C. for 5 days. (In case carbon source having 3 to 7 carbon atoms is used, the vessel is closed up tight.)

After the reaction, the products in the broth were separated, and then identified and quantified by gas-chromatography. The results are shown in Table 2.

Table 1

| Substrate | Produced 1,2-epoxides | yields (g/L) |
|---|---|---|
| Propylene | 1,2-epoxypropane | 0.77 |
| Butane-1 | 1,2-epoxybutane | 0.32 |
| Pentene-1 | 1,2-epoxypentane | 0.02 |
| Hexane-1 | 1,2-epoxyhexane | 0.012 |
| Heptene-1 | 1,2-epoxyheptane | 0.010 |
| Octene-1 | 1,2-epoxyoctane | 0.014 |
| Nonene-1 | 1,2-epoxynonane | 0.016 |
| Decene-1 | 1,2-epoxydecane | 0.016 |
| Undecene-1 | 1,2-epoxyundecane | 0.014 |
| Dodecene-1 | 1,2-epoxydodecane | 0.82 |
| Tridecene-1 | 1,2-epoxytridecane | 2.0 |
| Tetradecene-1 | 1,2-epoxytetradecane | 2.6 |
| Pentadecene-1 | 1,2-epoxypentadecane | 1.4 |
| Hexadecene-1 | 1,2-epoxyhexadecane | 1.0 |
| Heptadecene-1 | 1,2-epoxyheptadecane | 0.81 |
| Octadecene-1 | 1,2-epoxyoctadecane | 0.42 |
| Nonadecene-1 | 1,2-epoxynonadecane | 0.71 |
| Eicosene-1 | 1,2-epoxyeicosane | 0.20 |
| 1,13-tetradecadiene | 13,14-epoxy-1-tetradecene | 0.31 |

Table 2

| Substrate | Produced 1,2-epoxides | Yields (g/L) |
|---|---|---|
| Propylene | 1,2-epoxypropane | 0.53 |
| Butene-1 | 1,2-epoxybutane | 0.30 |
| Pentene-1 | 1,2-epoxypentane | 0.01 |
| Hexene-1 | 1,2-epoxyhexane | 0.10 |
| Heptene-1 | 1,2-epoxyheptane | 0.02 |
| Octene-1 | 1,2-epoxyoctane | 0.013 |
| Nonene-1 | 1,2-epoxynonane | 0.14 |
| Decene-1 | 1,2-epoxydecane | 0.24 |
| Undecene-1 | 1,2-epoxyundecane | 2.8 |
| Dodecene-1 | 1,2-epoxydodecane | 3.7 |
| 1,11-dodecadiene | 11,12-epoxy-1-dodecene | 0.16 |
| Tridecene-1 | 1,2-epoxytridecane | 3.8 |
| Tetradecene-1 | 1,2-epoxytetradecane | 4.2 |
| 1,13-tetradecadiene | (13,14-epoxy-1-tetradecene | 1.51 |
| | (1,2-13,14-diepoxytetradecane | 0.19 |
| Pentadecene-1 | 1,2-epoxypentadecane | 3.6 |
| Hexadecene-1 | 1,2-epoxyhexadecane | 2.7 |
| Heptadecene-1 | 1,2-epoxyheptadecane | 5.6 |
| Octadecene-1 | 1,2-epoxyoctadecane | 3.9 |
| Nonadecene-1 | 1,2-epoxynonadecane | 2.3 |
| Eicosene | 1,2-epoxyeicosane | 1.7 |

What is claimed is:

1. A method for manufacture of an epoxide from an olefin of the group consisting of α-olefins and α,ω-dienes having 4 to 20 carbon atoms which comprises culturing aerobically in a nutrient medium containing such olefin the organism Nocardia corallina, A.T.C.C. 31338 and separating the resulting epoxide therefrom.

2. A method for manufacture of an epoxide from an olefin of the group consisting of α-olefins and α,ω-dienes having 4 to 20 carbon atoms which comprises culturing the organism Nocardia corallina, A.T.C.C. 31338 in a nutrient medium containing an assimilable carbon source, harvesting the organism, allowing the organism to react aerobically with the olefin, and separating the resulting epoxide therefrom.

* * * * *